United States Patent [19]
Morrow et al.

[11] Patent Number: 5,656,242
[45] Date of Patent: Aug. 12, 1997

[54] AIR PURIFIER DEVICE

[75] Inventors: William Morrow; Larry James McLean, both of Stroud, Canada

[73] Assignee: L2B Environmental Systems Inc., Stroud, Canada

[21] Appl. No.: 482,830

[22] Filed: Jun. 7, 1995

[51] Int. Cl.$^6$ .................................................. A62B 7/08
[52] U.S. Cl. ........................... 422/121; 55/279; 422/120
[58] Field of Search ................................ 422/120, 121, 422/4, 5; 55/279; 96/16, 60

[56] References Cited

U.S. PATENT DOCUMENTS

| | | | |
|---|---|---|---|
| 3,094,400 | 6/1963 | Blanton | 96/16 |
| 3,403,252 | 9/1968 | Nagy | 422/121 X |
| 4,102,654 | 7/1978 | Pellin | 55/279 X |
| 4,694,179 | 9/1987 | Lew et al. | 250/431 |
| 5,112,370 | 5/1992 | Gazzano | 55/279 X |
| 5,230,220 | 7/1993 | Kang et al. | 422/121 X |

FOREIGN PATENT DOCUMENTS

| | | |
|---|---|---|
| 1063695 | 3/1967 | United Kingdom . |
| 1536397 | 12/1978 | United Kingdom . |
| 2215234 | 9/1989 | United Kingdom . |
| WO90/0590 | 5/1990 | WIPO . |

*Primary Examiner*—Robert J. Warden
*Assistant Examiner*—Krisanne M. Thornton
*Attorney, Agent, or Firm*—Renner, Otto, Boiselle & Sklar

[57] ABSTRACT

An air purifier has a perforated plate between UV lamps on the one hand and a porous air filter on the other. Biological material is trapped by the filter and eventually killed by the low dose of UV radiation which passes through the perforations in the plate. Filtered air passing through the plate is subjected to a high dose of UV radiation which sterilizes remaining biological material in the air. An electrostatic filter at the outlet may trap viruses which have been positively charged either by the action of the UV lamps or by positively charging the plate in order to strip electrons from the viruses. The UV lamps may be mercury lamps which are allowed to emit at both their ozone forming wavelength as well as the ozone breakdown wavelength. In such instance, a light filter surrounds the lamps which passes light only at the ozone breakdown wavelength. Air subjected to the unfiltered light is consequently subjected to ozone, which is a known biocide. The filtered light is in a zone which is filled with water mist such that hydroxyl radicals result. Air passing through this zone is scrubbed by the hydroxyl radicals.

17 Claims, 5 Drawing Sheets

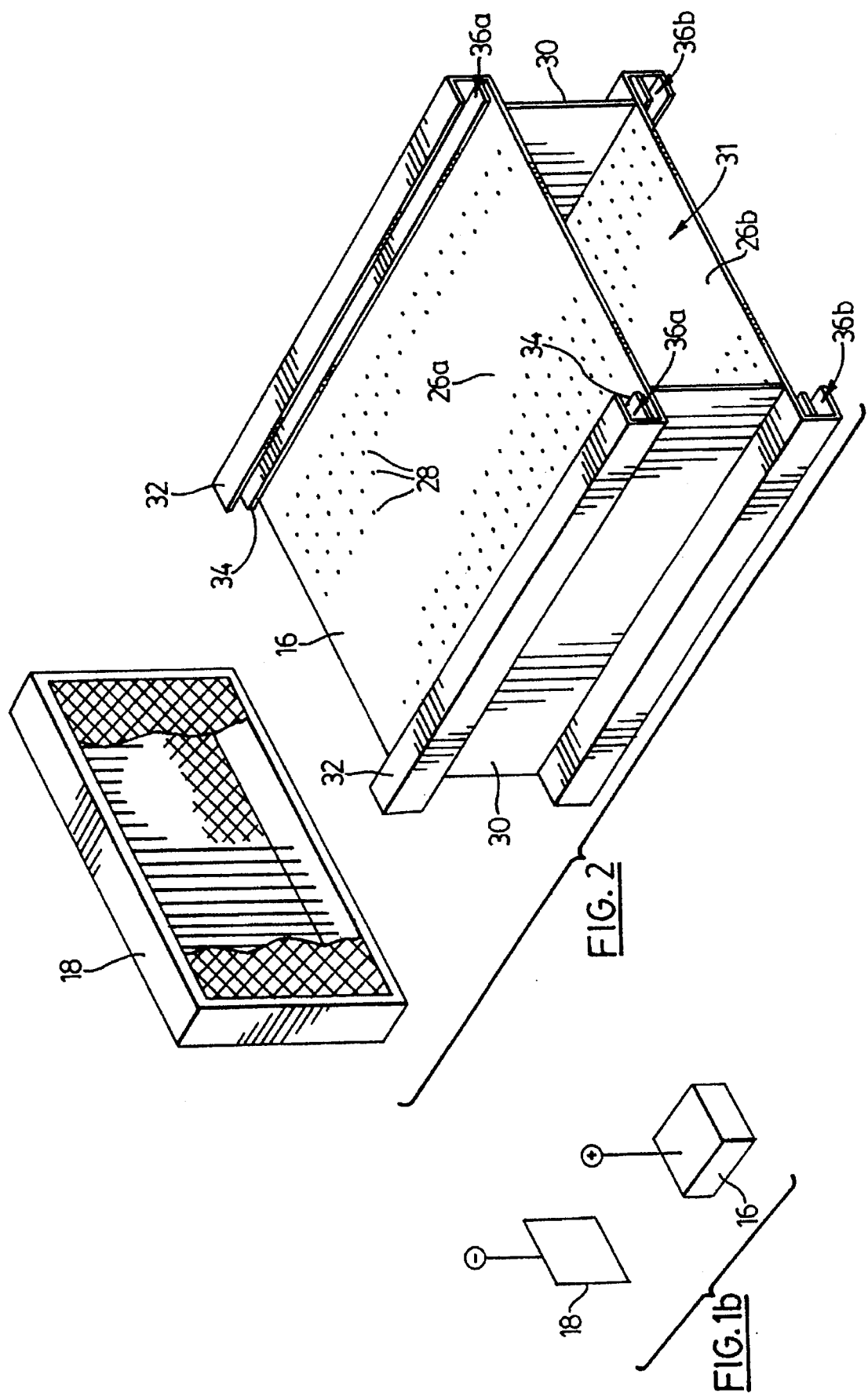

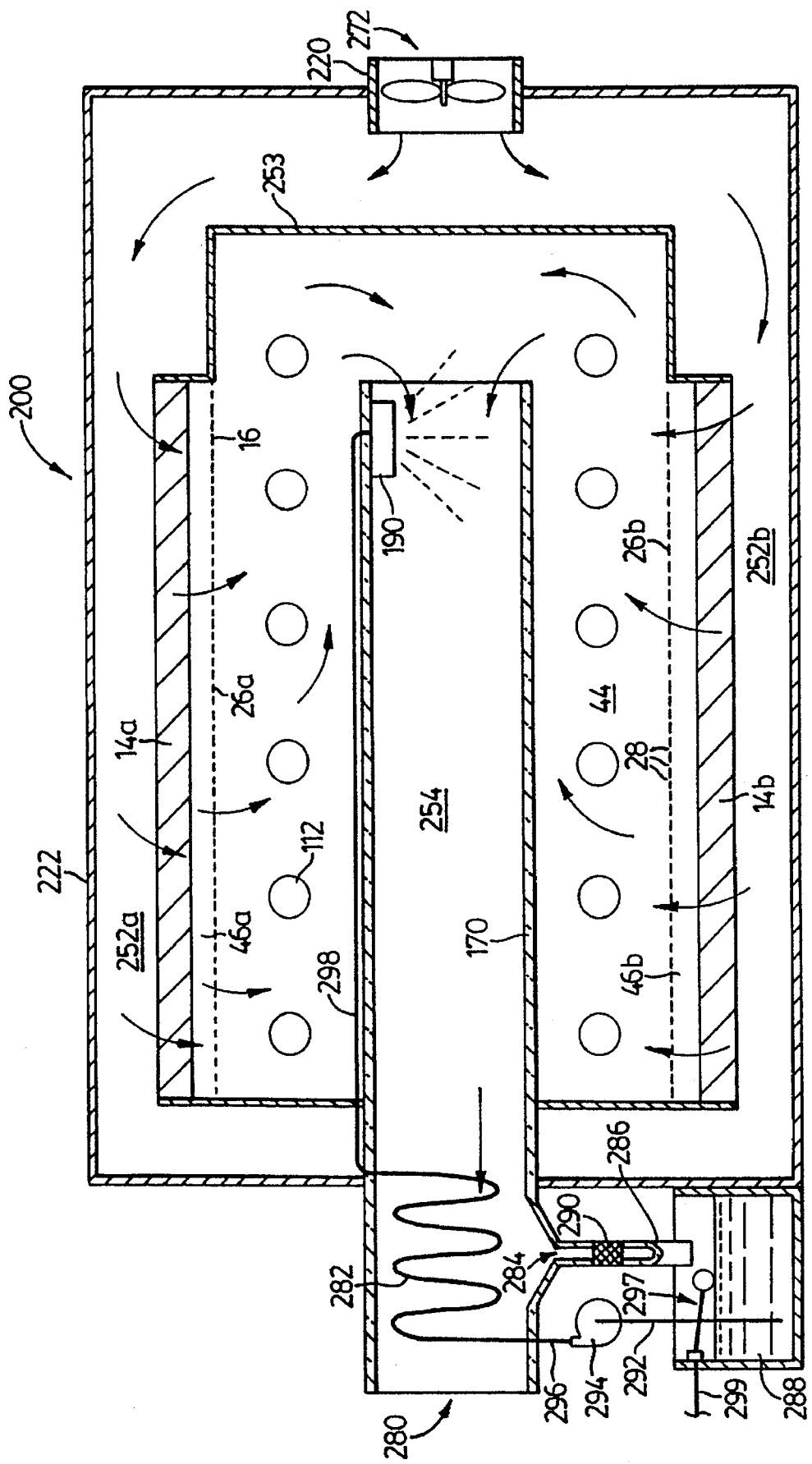

/ 1

AIR PURIFIER DEVICE

BACKGROUND OF THE INVENTION

1. Field of the Invention

This invention relates to an air purifier.

2. Description of the Related Art

It is known that ultraviolet ("UV") light sterilizes DNA so that biological material (such as viruses, bacteria, molds, yeasts, and pollens) exposed to UV light either dies or cannot reproduce. This property of UV light has been utilized to sterilize air in a building by simply placing UV lamps in the building's air ducts. One drawback with this approach is that biological material may not be exposed to UV light for a sufficient time to be sterilized. To address this drawback, it is known to utilize a porous air filter end mount a UV light for reciprocating movement across a face of the filter. In operation, a fan draws air through the filter resulting in biological material becoming trapped in the filter. The irradiation of the filter with the reciprocating UV light acts to kill this trapped biological material. However some biological material, namely viruses, readily pass through porous filters and would not, therefore, be sterilized with the combination of a porous filter in conjunction with a UV lamp. Furthermore, UV light degrades a porous filter requiring frequent replacement of same.

Ozone is a known biocide. However, due to its dangers to humans, it has not found wide application in killing bacteria and the like in air.

The present invention seeks to overcome drawbacks of the known prior art.

SUMMARY OF THE INVENTION

According to the present invention, there is provided an air purifier, comprising, e source of ultraviolet radiation for emitting light along a light path; an air filter disposed in said light path; a wall disposed in said light path between said source of ultraviolet radiation and salad air filter; said wall having a plurality of light transmissive air passageways extending therethrough so that said wall is partially transmissive to ultraviolet light; said wall being partially reflective of ultraviolet light member being partially transmissive to ultraviolet light and partially reflective of ultraviolet light, said member arranged to permit the passage of air.

According to another aspect of the invention, there is provided an air purifier comprising, a source of ultraviolet light chosen from a class of sources which emit radiation along a light path at a first wavelength which forms ozone and at a second wavelength which breaks down ozone; a light filter absorbing of light at said first wavelength and transmissive to light at said second wavelength, said light filter disposed in a path of light from said source of ultraviolet light so as to form an ozone forming zone extending from a side of said light filter upon which light from said source of ultraviolet light is incident and an ozone breakdown zone extending from a side of said light filter opposite said light incident side; said ozone forming zone being in fluid communication with said ozone breakdown zone; a water mister disposed in said ozone breakdown zone; an air inlet in fluid communication with said ozone forming zone and an air outlet in fluid communication with said ozone breakdown zone.

BRIEF DESCRIPTION OF THE DRAWINGS

FIG. 1b is a schematic view of a portion of the purifier of FIG. 1, FIG. 2 is an exploded view of two components of the air purifier of FIG. 1, FIG. 5 is a simplified cross-sectional side view of an air purifier made in accordance with a further aspect of this invention.

DETAILED DESCRIPTION OF THE PREFERRED EMBODIMENTS

Figure 1:
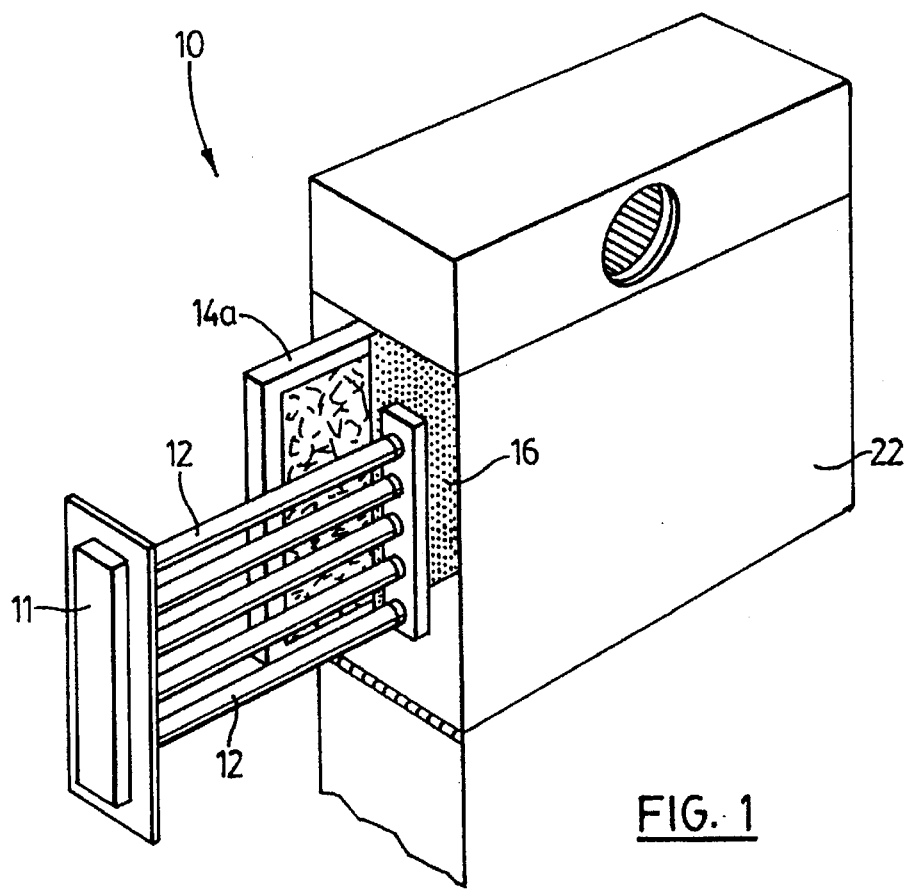
FIG. 1 is a perspective partially exploded view of an air purifier made in accordance with this invention.
Figure 4:
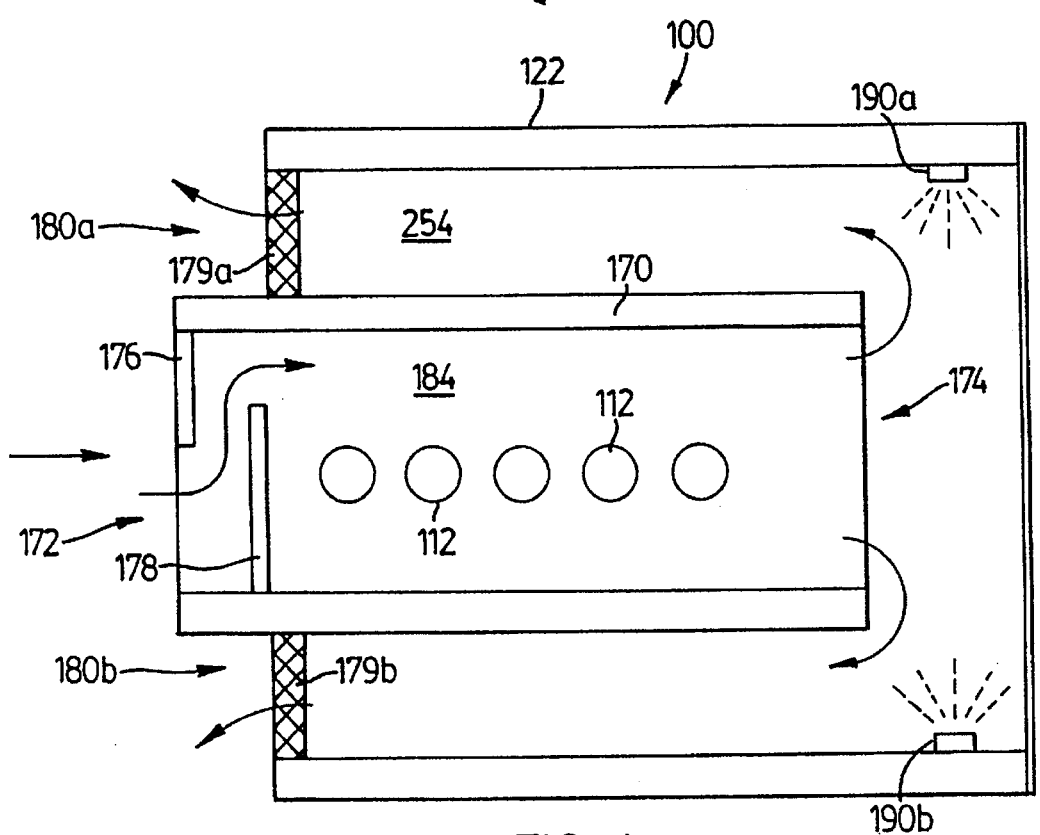

Turning to FIGS. 1, 1a, 2 and 3, an air purifier 10 made in accordance with this invention comprises a source of ultraviolet radiation in the nature of ballast 11 powered UV lamps 12, porous air filters 14a, 14b, a member 16, an electrostatic filter element 18, and a blower 20 all contained within housing 22. The electrostatic filter element 18 comprises an electrically charged grid.

As seen in FIG. 2, member 16 has plate-like side walls 26a, 26b with a plurality of light transmissive air passageway 28 therethrough. Member 16 also has top and bottom walls 30 connected to the side walls 26a, 26b in order to form a box-like cavity 31 within the walls.

Separate pairs of flanges 32, 34 form opposed channels 36a spaced from side wall 26a and opposed channels 36b spaced from side wall 26b. Channels 36a receive porous air filter 14a and support it with a small standoff from side wall 26a. Similarly, channels 36b receive porous air filter 14b (FIG. 3) such that filter 14b has a small standoff from side wall 26b.

The light transmissive air passageways 28 cover about 5% of the surface of walls 26a and 26b. The side walls 26a, 26b end top end bottom walls 30 have highly reflective inner surfaces. This may be achieved by fabricating member 16 from a reflective metal or coating its inner surface with a highly reflective multi-layer dielectric coating or paint. In the result, with lamps 12 activated, some light will pass through passageways 28 but most will be reflected back by the inner surfaces of member 16. Consequently, member 16 is partially transmissive to ultraviolet light from lamps 12 and partially reflective of ultraviolet light from these lamps.

Figure 3:
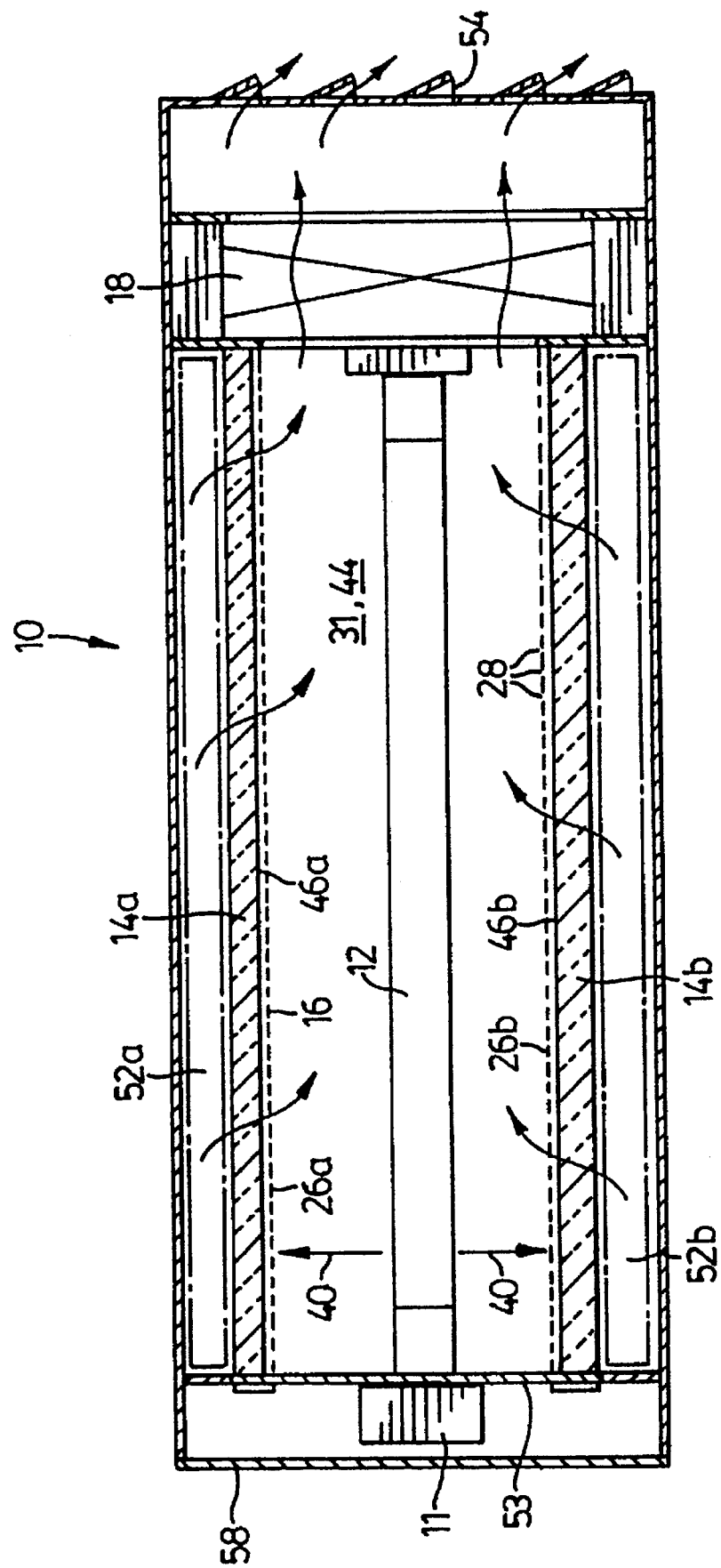
FIG. 3 is a cross-sectional view along the lines III—III of FIG. 1a, FIG. 4 is a schematic side view of an air purifier made in accordance with another aspect of this invention.

Referring to FIG. 3, with lamps 12 activated, light will be directed outwardly from the lamps along light paths 40. All light incident upon the inner surfaces of top and bottom walls 30 and most light incident upon the inner surface of side walls 26a, 26b will be reflected. Thus, a primary radiation zone 44 is formed within the cavity 31 formed by the walls of member 16. Due to light transmissive air passageways 28, some light will pass through the wall 26a of member 16 into the zone 46a wall 26a and filter 14a resulting from the standoff of the filter 14a from the wall 26a. This transmitted light will impinge upon filter 14a. Similarly, some light will pass through passageways 28 in wall 26b into the zone 46b between Wall 26b of member 16 and filter 14b and impinge upon filter 14b. Since zones 46a, 46b receive a relatively small proportion of the light from light sources 12, these zones may be referred to as secondary radiation zones.

Figure 1A:
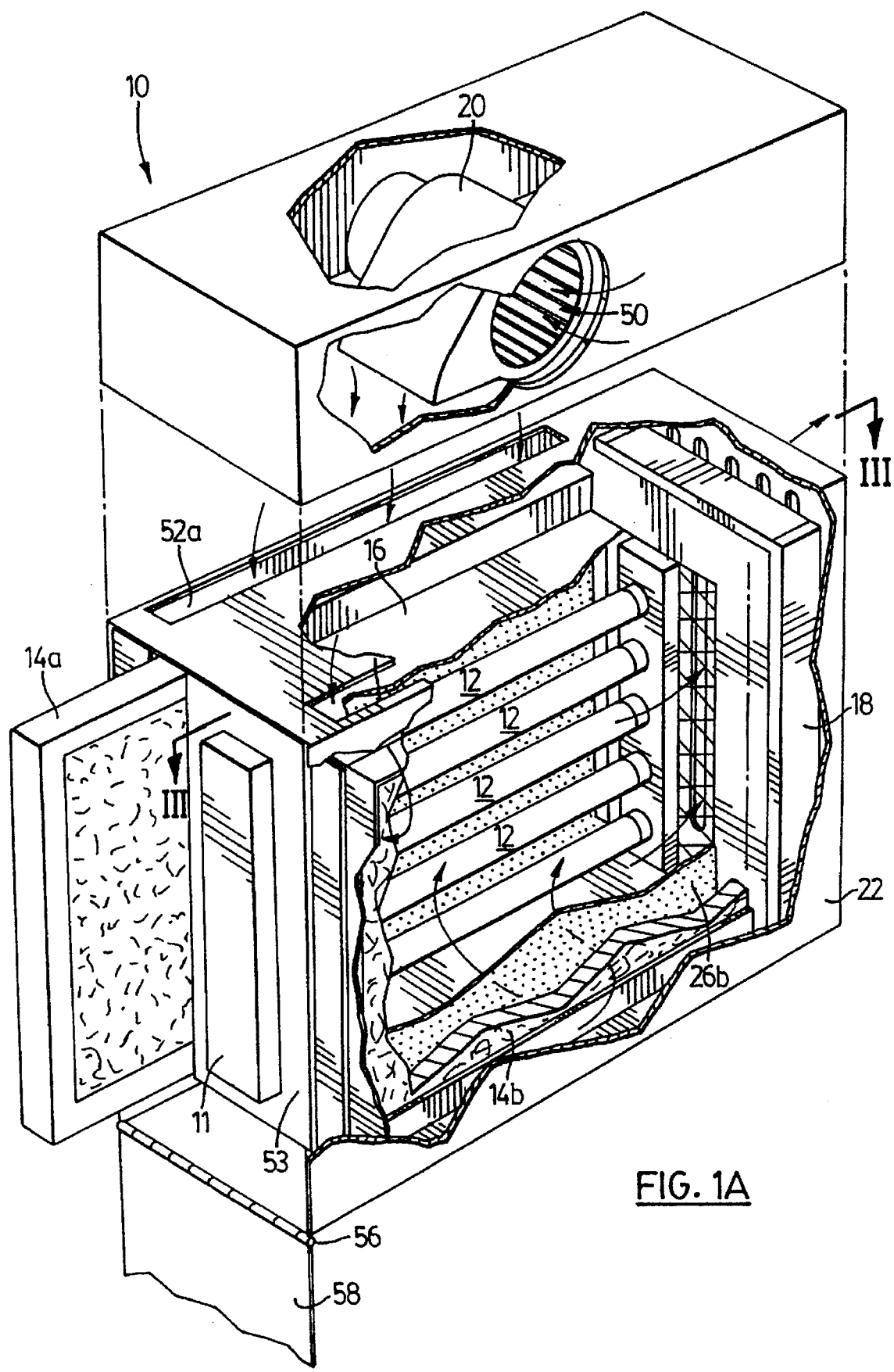
FIG. 1a is a perspective view of the purifier of FIG. 1 partially in phantom and partially broken away.

Referencing FIGS. 1a and 3, blower 20 is disposed between an air inlet 50 and cavities 52a, 52b. Ballast plate 53 closes one end of the cavity 31 formed by the walls of member 16. The other end of this cavity communicates with a louvred air outlet 54 through electrostatic filter element 18. The housing 22 has a flap 58 which may be hinged about hinge 56 to close the end of the housing.

In operation, when blower 20 is activated, air is drawn into inlet 50, end blown out into cavities 52a, 52b. From there the air passes through porous filters 14a and 14b and through air passageways 28 in member 16 into the primary radiation zone 44. The air is the in free to flow out of zone 44 through electrostatic filter element 18 and exit through louvred outlet 54.

With lamps 12 activated, light travels along pathways 40 and is reflected by the inner surface of the walls of member 16 so that member 16 recycles the reflected photons. A large enhancement of the optical UV flux density in the primary radiation zone 44 formed by member 16 is possible since photons reflected by this member are minimally absorbed by the filtered air entering This zone. Some light passes through the light transmissive air passageways 28 into the secondary radiation zones 46a and 46b and impinges upon filters 14a, 14b.

As air passes through porous filters 14a, 14b, larger particles of biological material such as bacteria, molds and pollens in the air will become trapped in the filters. This trapped biological material will be subjected to a low but constant dose of UV radiation such that over time this biological material will be sterilized. Biological material which remains in the air and passes into the primary radiation zone 44 will be subjected to a high level of UV radiation and, therefore, will receive a high UV dose. Thus, much of the virus material in air passing into The primary radiation zone will be sterilized.

Due to the photo electric effect, UV light can strip an electron from each virus in the primary radiation zone 44 and therefore positively charge the viruses. The magnitude of this effect will be dependent on the quantum efficiency of the virus particles. This quantity is the ratio of photoionizing photons to the total photons incident on a virus. In this invention this photoionization is enhanced by the recycling of light in the primary radiation zone. As is apparent from FIG. 1b, electrostatically charged filter element 18 is negatively charged. Consequently, positively charged viruses exiting zone 44 through the filter element 18 will be trapped by the electrostatic filter 18. A small amount of UV radiation will fall on filter element 18 such that viruses trapped in this filter will also eventually be sterilized.

It is expected that, again due to the photo electric effect, UV light impinging on metal member 16 will cause electrons to be ejected from the member. It is believed this will form an electron cloud within the primary radiation zone 44. This electron cloud may trap positively charged viruses within the primary radiation zone for a period of time sufficient to allow these viruses to be sterilized by the UV light.

Optionally, metal member 16 may be positively charged, as indicated in FIG. 1*b*. If air passageways 28 are also made very small, the resulting hydrodynamic forces should cause an air flow which will improve the exposure of the viruses to member 16. With this arrangement, many viruses will lose an electron to the positively charged metal member. Consequently, this will increase the proportion of viruses which are positively charged in zone 44.

Purified air passing filter element 18, leaves the unit 10 via outlet 54.

UV light will degrade a porous filter. However, with the purifier 10, the UV light impinging on porous air filters 14*a*, 14*b* is relatively small so that filter life is greatly enhanced.

In order to change filters 14*a*, 14*b* or replace any of lamps 12, flap 58 may be swung open about hinged connection 56. The filters 14*a*, 14*b* may then easily be removed by sliding same from channels 36*a*, 36*b* of member 16. Also, the lamp assembly may then be simply withdrawn from within the cavity 31 of member 16.

As an alternative to utilizing ballast powered lamps, the lamps may be RF powered. This is advantageous since the air purifier is completely enclosed thereby avoiding any possible health concerns related to RF leakage and since RF powered lamps may be more energy efficient end longer lived than normal ballast powered lamps.

Optionally, member 16 could be extended laterally and the UV lamps 12 lengthened with the result that the primary radiation zone is extended. With this arrangement, all incoming air would be directed through the filters, however, air would then be free to pass into the primary radiation zone anywhere along the length of the secondary radiation zones. The increased number of passageways into the primary radiation zone would decrease back pressure.

As a further option, blower 20 could be positioned at outlet 54 so as to draw air through the purifier. It will be appreciated that, in such instance, the purifier could be designed so that it exhausts out its bottom wall, with its air inlet remaining through its top wall.

Turning to FIG. 4 which illustrates another embodiment of this invention, air purifier 100 comprises a source of ultraviolet light in the nature of UV lamps 112. The UV lamps are mercury lamps which emit light at two wavelengths, 184 nm and 254 nm. While this is the standard emission spectra for mercury lamps, the 184 nm emission in standard mercury lamps is blocked since 184 nm light in the presence of oxygen forms ozone and ozone is a known biocide which is deleterious to humans 184 nm light is blocked in standard mercury lamps even though 254 nm light breaks down ozone into oxygen and an excited oxygen radical because the excited oxygen radical will normally recombine with oxygen to again form ozone.

A light filter 170 surrounds lamps 112 but leaves an air inlet 172 and an air outlet 174. The inlet 172 is provided with light absorbing opaque baffles 176, 178 which provide a tortuous path through the inlet such that light emitted from lamps 112 cannot pass through the inlet to the exterior of purifier 100. Light filter 170 absorbs light at 184 nm and is transmissive to light at 254 nm. Housing 122 surrounds light filter 170 so as to direct air exiting from outlet 174 of the light filter back along the outside surface of the light filter to filters 179*a*, 179*b* at outlets 180*a*, 180*b*, respectively. The housing 122 supports internally directed water misters 190*a*, 190*b*. The interior Surface of housing 122 is made of a light reflective material.

In operation, air is passed through the purifier 100 from the inlet 172 to the outlets 180*a*, 180*b*. With lamps 112 activated, light will be directed along the light path 182 passing through the filter 170. The resulting 184 nm light in the zone 184 between lamps 112 and filter 170 will form ozone in this zone (which, as aforenoted, will not be eliminated by the 254 nm light). The ozone acts as a biocide killing biological material, such as bacteria, molds and the like in the air. The only light in zone 254 between the light filter 170 and housing 122 will be at 254 nm. This light initially breaks down the ozone exiting from zone 184 into oxygen and excited oxygen radical. However, with misters 190*a*, 190*b* operating, the excited oxygen radicals will be exposed to water end will combine with same to form hydroxyl radicals. Thus, in zone 254, ozone will be broken down into oxygen gas and hydroxyl radicals. Therefore, when air leaves the ozone formation zone 184 and enters the ozone breakdown zone 254, the air is subjected to hydroxyl radicals. hydroxyl radicals are a known primary scrubbing glass thus, for example, hydroxyl radicals in the presence of carbon monoxide result in carbon dioxide. Similarly, hydroxyl radicals combine with sulphur dioxide to form sulphur trioxide. These gases are removed by filters 179a, 179b, which may be molecular seine filters. Therefore, in ozone breakdown 254, air is purified of pollutants. It will also be recognised by those skilled in the art that peroxides formed by the hydroxyl radicals are biocides. Therefore, these peroxides assist in killing any living biological material which may reach zone 254. Consequently, leaving outlets 180a, 180b has not only been sterilized, but has also been de-toxified.

A practical problem with water misters is the large mass of water required to humidify air. This probably means the units 100 would have to be combined with the humidifier systems of whatever building they were in. One place where this problem is not so large is in a car or other enclosed space. One could see how such a device would be extremely beneficial during rush hour when CO concentrations in traffic approach toxic levels. The car enclosure is ideal since human breathing will humidify the air.

Turning to FIG. 5 which illustrates a further embodiment of the invention, like parts of purifier 200 to those of purifier 10 end purifier 100 have been given like reference numerals. Purifier 200, is in large part, a combination of purifier 10 and purifier 100. Light sources 112 emit UV light at 184 nm and 254 nm. Porous air filters 14a, 14b are supported by member 16 in spaced relation to the side wall 26a of member 16 and the side wall 26b of member 16, respectively. A tubular light filter 170 is positioned between lamps 112 and internally supports a mister 190. A blower 220 acts to draw air in through inlet 272 and this air is then deflected by baffle 253 into cavities 252a, 252b. The air then passes from these cavities through air filters 14a, 14b and through the light transmissive air passageways 28 in member 16 into zone 44. Air then exits from zone 44 into zone 254 within the light filter 170 and from there past condenser coil 282 to outlet 280. A drain 284 is positioned below the condenser coil and a drain pipe 286 leads from the drain to a reservoir 288. A filter 290 is disposed In the drain pipe. An intake pipe 292 to a pump 294 is positioned in the reservoir. The pump outlet 296 feeds the condenser coil 282 end an outlet pipe 298 from the condenser coil inputs the mister 190. A float valve 297 selectively admits water from pressurised water supply pipe 299 to the reservoir.

With the blower causing air to flow through the purifier, larger particles of biological material in air travelling through porous air filters 14a, 14b are trapped within the filters. This trapped material is subjected to a low doze of constant UV radiation by lamps 112, which radiation has passed through the light transmissive air passageways 28 end the secondary radiation zones 46a, 46b. When the filtered air reaches the primary radiation zone 44, remaining biological material in the air is subjected to a high dose of radiation and, therefore, a high kill rate. Additionally, due to the emission at 184 nm from lamps 112, ozone is formed in gone 44 and this ozone acts as a biocide killing additional biological material in the air. Air exiting zone 44 into zone 254 is subjected to hydroxyl radicals and peroxides formed in zone 254 which scrubs pollutants from the air. The volume of water injected into zone 254 is chosen such that the air in zone 254 remains humid. Consequently, pollutants scrubbed from the air will tend to dissolve in the water mist.

The water mist is largely condensed as the air passes over condenser coil 282 so that the condensed water, with dissolved pollutants, falls into drain 284. Thus, air exiting outlet 280 is sterilized end detoxified.

Condensed water entering drain 284 passes along drain pipe 286 through filter 290. The filter filters the dissolved pollutants from the water so that purified water enters reservoir 288. Pump 294 pumps water from the reservoir through the condenser coil to mister 190 so that water is re-circulated in the system. Since some water mist will pass through outlet 280, float valve 297 admits additional water to the reservoir.

A number of the purifiers 10, 100 or 200 could be placed in strategic locations in a building in order to purify air in the building. Alternatively, a number of elf intakes may be provided in the ceiling of a room which lead to a purifier. The volume of air which is admitted by an intake may be controlled manually at the intake or remotely with, for example, an infrared sensor at the intake which is responsive to an infrared wand or which senses the presence or a person below the intake. In, for example, a doctor's waiting room with chairs along three walls, a U-shaped tube could extend along the ceiling adjacent these three walls above the waiting room chairs. The U-shaped tube may be provided with air inlets in its base above each chair. The centre of the U-shape may have an extension to the inlet of an air purifier supported on the ceiling at the centre of the room. The purifier is placed with its outlet directed into the room.

An air purifier of this invention could be incorporated into a heating furnace for a building. In such case, no blower is needed in the purifier as the furnace fan provides for air flow through the purifier. Other modifications Will be apparent to those skilled In the art and, accordingly, the invention is defined in the claims.

What is claimed:

1. An air purifier, comprising:

a source of ultraviolet radiation for emitting light along a light path;

an air filter disposed in said light path;

a wall disposed in said light path between said source of ultraviolet radiation and said air filter;

said wall having a plurality of light transmissive air passageways extending therethrough so that said wall is partially transmissive to ultraviolet light;

said wall being partially reflective of ultraviolet light.

2. The air purifier of claim 1 wherein said wall has an inner surface facing said source of ultraviolet radiation and said passageways comprise about 5% of said inner surface.

3. The air purifier of claim 2 including a blower for blowing air through said air filter, and through said wall.

4. The air purifier of claim 3 including means to positively charge said wall.

5. The air purifier of claim 4 wherein said air filter is a porous filter.

6. An air purifier comprising:

a source of ultraviolet light;

a walled member at least substantially surrounding said source of ultraviolet light so as to define a primary irradiation zone between said source of ultraviolet light and an inner surface of said walled member, said walled member having a plurality of light transmissive air passageways extending from said inner surface to an opposed outer surface of said walled member;

an air filter disposed so that light emitted by said source of ultraviolet radiation which passes through said light transmissive air passageways of said walled member impinges on said air filter, said walled member outer surface and said air filter defining a secondary irradiation zone therebetween;

said walled member being partially reflective of ultraviolet light such that light emitted by said source of ultraviolet light may be reflected by said walled member back into said primary irradiation zone.

7. The air purifier of claim 6 wherein said passageways comprise about 5% of said inner surface.

8. The air purifier of claim 6 including an air inlet disposed on a side of said air filter opposite said secondary irradiation zone and an electrically negatively charged element disposed between an air outlet of said purifier and said primary irradiation zone so as to be exposed to light from said source of ultraviolet radiation.

9. The air purifier of claim 8 wherein said element comprises a grid.

10. The air purifier of claim 6 including means to positively charge said walled member.

11. The air purifier of claim 6 wherein said source of ultraviolet radiation is constructed to emit radiation at a first wavelength which forms ozone and at a second wavelength which breaks down ozone, said purifier including a light filter absorbing of light at said first wavelength and transmissive to light at said second wavelength and a water mister, said light filter disposed in a path of light from said source between said primary irradiation zone and an air outlet, said water mister disposed on a side of said light filter opposite a side upon which light from said light source is incident, said light filter defining a misting zone between said primary irradiation zone and said outlet, said misting zone being in fluid communication with said primary irradiation zone.

12. The air purifier of claim 11 including an air inlet disposed on a side of said air filter opposite said secondary irradiation zone and a blower for blowing air from said air inlet to said air outlet.

13. The air purifier of claim 11 wherein said source of ultraviolet light comprises a mercury lamp.

14. The air purifier of claim 11 wherein said air filter is a porous filter.

15. An air purifier comprising:

a source of ultraviolet light constructed to emit radiation along a light path at a first wavelength which forms ozone and at a second wavelength which breaks down ozone;

a light filter absorbing of light at said first wavelength and transmissive to light at said second wavelength, said light filter disposed in a path of light from said source of ultraviolet light so as to form an ozone forming zone extending from a side of said light filter upon which light from said source of ultraviolet light is incident and an ozone breakdown zone extending from a side of said light filter opposite said light incident side;

said ozone forming zone being in fluid communication with said ozone breakdown zone;

a water mister disposed in said ozone breakdown zone;

an air inlet in fluid communication with said ozone forming zone and an air outlet in fluid communication with said ozone breakdown zone.

16. The air purifier of claim 15 wherein said source of ultraviolet light comprises a mercury lamp.

17. The air purifier of claim 16 including a blower for blowing air from said air inlet, through said ozone forming zone and through said ozone breakdown zone to said air outlet.

* * * * *